(12) United States Patent
Davydov et al.

(10) Patent No.: US 10,463,260 B1
(45) Date of Patent: Nov. 5, 2019

(54) HEART DISEASE RISK ASSESSMENT

(71) Applicant: AURA Devices, Inc., Wilmington, DE (US)

(72) Inventors: Dmitrii Davydov, Lublin (PL); Andrey Boev, Stariy Oskol (RU)

(73) Assignee: AURA DEVICES, INC., Wilmington, DE (US)

( * ) Notice: Subject to any disclaimer, the term of this patent is extended or adjusted under 35 U.S.C. 154(b) by 0 days.

(21) Appl. No.: 16/405,553

(22) Filed: May 7, 2019

(51) Int. Cl.
| | | |
|---|---|---|
| *A61B 5/02* | (2006.01) | |
| *A61B 5/0295* | (2006.01) | |
| *A61B 5/04* | (2006.01) | |
| *A61B 5/024* | (2006.01) | |
| *A61B 5/11* | (2006.01) | |
| *G16H 50/30* | (2018.01) | |
| *A61B 5/08* | (2006.01) | |

(52) U.S. Cl.
CPC ...... *A61B 5/02405* (2013.01); *A61B 5/02007* (2013.01); *A61B 5/02416* (2013.01); *A61B 5/1118* (2013.01); *A61B 5/02028* (2013.01); *A61B 5/08* (2013.01); *A61B 5/1114* (2013.01); *A61B 5/1116* (2013.01); *A61B 2562/0219* (2013.01); *G16H 50/30* (2018.01)

(58) Field of Classification Search
None
See application file for complete search history.

(56) References Cited

PUBLICATIONS

Al-Zaiti SS, Pietrasik G, Carey MG, Alhamaydeh M, Canty JM, Fallavollita JA. The role of heart rate variability, heart rate turbulence, and deceleration capacity in predicting cause-specific mortality in chronic heart failure. J Electrocardiol 2019; 52:70-74.

Baccalá, L. A., & Sameshima, K. (2001). Partial directed coherence: a new concept in neural structure determination. Biological Cybernetics, 84(6), 463-474.

Bernardi L, Valle F, Coco M, Calciati A, Sleight P. Physical activity influences heart rate variability and very-low-frequency components in Holter electrocardiograms. Cardiovasc Res 1996; 32:234-7.

Buchheit M, Simon C, Viola AU, Doutreleau S, Piquard F, Brandenberger G. Heart rate variability in sportive elderly: relationship with daily physical activity. Med Sci Sports Exerc 2004; 36:601-5.

(Continued)

*Primary Examiner* — Brian T Gedeon
(74) *Attorney, Agent, or Firm* — Georgiy L. Khayet

(57) ABSTRACT

Systems and methods for heart disease risk assessment are described herein. An example method may comprise providing a first signal indicative of a heart rate variation (HRV) and respiration of a user, providing a second signal indicative of a HRV, respiration, and motion of the user, continuously determining a state function, wherein the state function depends on the HRV and the respiration, receiving an indication of a change of a body position of the user or a change of external conditions, in response to the indication, determining a shape of distortion of the state function, performing an analysis of the shape of distortion to determine at least one sign of a risk of the heart failure, and providing at least one alert or message regarding the at least one sign of the risk of the heart failure. The state function can include a coherence between the HRV and the respiration.

20 Claims, 7 Drawing Sheets

(56) References Cited

PUBLICATIONS

Dantas EM, Kemp AH, Andreäo RV, Da Silva VJD, Brunoni AR, Hoshi RA, et al. Reference values for short-term resting-state heart rate variability in healthy adults: Results from the Brazilian Longitudinal Study of Adult Health—ELSA-Brasil study. Psychophysiology 2018; 55:e13052.

Davydov DM, Zhdanov RI, Dvoenosov VG, Kravtsova OA, Voronina EN, Filipenko ML. Resilience to orthostasis and haemorrhage: A pilot study of common genetic and conditioning mechanisms. Sci Rep 2015; 5:10703.

Dick TE, Hsieh Y-H, Dhingra RR, Baekey DM, Galan RF, Wehrwein E, et al. Cardiorespiratory coupling: common rhythms in cardiac, sympathetic, and respiratory activities. Prog Brain Res 2014; 209:191-205.

Faes L, Nollo G, Porta A. Information domain approach to the investigation of cardio-vascular, cardio-pulmonary, and vasculo-pulmonary causal couplings. Front Physiol 2011; 2:80.

Galinier M, Pathak A, Fourcade J, Androdias C, Curnier D, Vamous S, et al. Depressed low frequency power of heart rate variability as an independent predictor of sudden death in chronic heart failure. Eur Heart J 2000; 21:475-482.

Guo Y, Palmer JL, Strasser F, Yusuf SW, Bruera E. Heart rate variability as a measure of autonomic dysfunction in men with advanced cancer Eur J Cancer Care (Engl) 2013; 22:612-6.

Hochstadt A, Chorin E, Viskin S, Schwartz AL, Lubman N, Rosso R. Continuous heart rate monitoring for automatic detection of atrial fibrillation with novel bio-sensing technology. J Electrocardiol 2019; 52:23-27.

Johansen CD, Olsen RH, Pedersen LR, Kumarathurai P, Mouridsen MR, Binici Z, et al. Resting, night-time, and 24 h heart rate as markers of cardiovascular risk in middle-aged and elderly men and women with no apparent heart disease. Eur Heart J 2013; 34:1732-1739.

La Rovere MT, Pinna GD, Maestri R, Mortara A, Capomolla S, Febo O, et al. Short-Term Heart Rate Variability Strongly Predicts Sudden Cardiac Death in Chronic Heart Failure Patients. Circulation 2003; 107:565-570.

Nolan J, Batin PD, Andrews R, Lindsay SJ, Brooksby P, Mullen M, et al. Prospective Study of Heart Rate Variability and Mortality in Chronic Heart Failure. Circulation 1998; 98:1510-1516.

Park J, Lee S, Jeon M. Atrial fibrillation detection by heart rate variability in Poincare plot. Biomed Eng Online 2009; 8:38.

Patel VN, Pierce BR, Bodapati RK, Brown DL, Ives DG, Stein PK. Association of Holter-Derived Heart Rate Variability Parameters With the Development of Congestive Heart Failure in the Cardiovascular Health Study. JACC Hear Fail 2017; 5:423-431.

Porta A, D'Addio G, Bassani T, Maestri R, Pinna GD. Assessment of cardiovascular regulation through irreversibility analysis of heart period variability: a 24 hours Holter study in healthy and chronic heart failure populations. Philos Trans A Math Phys Eng Sci 2009; 367:1359-1375.

Rajendra Acharya U, Paul Joseph K, Kannathal N, Lim CM, Suri JS. Heart rate variability: A review. Med Biol Eng Comput 2006; 44:1031-1051.

Santos M, West E, Skali H, Forman DE, Nadruz W, Shah AM. Resting Heart Rate and Chronotropic Response to Exercise: Prognostic Implications in Heart Failure Across Left Ventricular Ejection Fraction Spectrum. J Card Fail 2018; 24:753-762.

Tamaki S, Yamada T, Okuyama Y, Morita T, Sanada S, Tsukamoto Y, et al. Cardiac Iodine-123 Metaiodobenzylguanidine Imaging Predicts Sudden Cardiac Death Independently of Left Ventricular Ejection Fraction in Patients With Chronic Heart Failure and Left Ventricular Systolic Dysfunction. Results From a Comparative Study With Si. J Am Coll Cardiol 2009; 53:426-435.

Thayer JF, Yamamoto SS, Brosschot JF. The relationship of autonomic imbalance, heart rate variability and cardiovascular disease risk factors. Int J Cardiol 2010; 141:122-131.

HEART DISEASE RISK ASSESSMENT

TECHNICAL FIELD

The present disclosure relates generally to health monitoring, more particularly, to systems and methods for heart disease risk assessment.

BACKGROUND

The cardiovascular system consists of the heart, blood vessels, and blood. One of the major functions of the cardiovascular system is providing nutrients and oxygen to organs and tissues of a human body and removing metabolic wastes from the organs and tissues. During rest (low arousal condition) and stress (high arousal condition) associated with various changes in an ambient environment, the amount of nutrients and oxygen needed by tissues and organs may change. The body may adapt to the changes by adjusting the volume of blood pumped per unit of time, volume and frequency of inhaled and exhaled air, and respiration rate. The loss of capacity of the organism to adapt to the low arousal condition and the high arousal condition may be indicative of a predisposition to diseases or even an early stage of one or more diseases, and a risk of death.

Heart rate variability (HRV) may include data concerning adaptive capacity of the organism. Some current medical and fitness devices analyze the HRV in order to detect a health problem or to issue recommendations on training regimes. However, the current medical and fitness devices do not provide an accurate estimate of the risk of development of diseases, since they do not perform a rigorous analysis of the HRV. In most cases, the current analysis is limited to detection that the HRV (and other vital sign parameters) are outside pre-determined magnitude and frequency ranges obtained from population studies. The current analysis may also include determining that the HRV and other vital sign parameters are within magnitude and frequency ranges obtained in clinical studies performed without control of origin of the HRV. However, the individual features of each human organism may introduce uncertainty in the assessment of the boundaries of HRV associated with breathing, vascular, muscle, and other activities as a measure of healthy conditions. As a result, the current medical and fitness devices lack reliability of the assessment of health conditions of the human organism and prognosis of risk of heart disease, such as heart failure, atrial fibrillation, and cardiac arrest in a particular individual.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are systems and methods for heart disease risk assessment. Some embodiments of the present disclosure may allow determination of the risk of development of a heart failure at asymptomatic stage. Some embodiments of the present disclosure may provide a wearable device for heart disease risk assessment.

According to one example embodiment, a system for heart disease risk assessment is provided. The system may include a first sensor configured to provide a first signal indicative of an HRV and respiration of a user. The system may further include a second sensor configured to provide a second signal indicative of a HRV, respiration, and movement of the user. The system may further include a controller communicatively coupled to the first sensor and the second sensor. The controller can be configured to continuously determine, based on the first signal and the second signal, a state function. The state function may depend on the HRV and the respiration. The controller may further receive an indication of one of a change of a body position of the user or a change of one or more external conditions like ambient light, noise, humidity, or altitude. In response to the indication, the controller may further determine a shape of a distortion of the state function, wherein the distortion is caused by the change of the body position or the change of the one or more external conditions. The controller may further perform an analysis of the shape of the distortion to determine at least one sign of a risk to heart failure. In response to the determination of the at least one sign of the heart failure, the controller may further provide, via an alert unit communicatively coupled to the controller, at least one alert or message regarding the sign of the heart failure.

The state function may include a coherence of the HRV with respect to the respiration with the assessment of a phase and transfer function gain. The first sensor may include a photoplethysmography (PPG) sensor configured to be contactable with a body of the user. The first signal may include a PPG signal. The first sensor may include a bioimpedance (BI) sensor configured to be contactable with a body of the user and the first signal may include a BI signal. The second sensor may include a motion sensor configured to detect motion, heart beating, and breathing of the user. The motion sensor may include a gyroscope, a magnetometer, or an accelerometer. The first sensor and the second sensor can be integrated in a wearable device configured to be disposed on a body of the user.

The analysis of the shape of distortion may include determining, based on the shape of distortion, a level an of the distortion of the state function and comparing the level of distortion to a pre-defined threshold. The pre-defined threshold can be determined based on a shape of normal distortion of a state function in response to a change of one or more external conditions like ambient light, noise, humidity, or altitude. The normal distortion of the state function can be measured for a healthy person.

The change of one or more external conditions may include one of the following: a change in ambient temperature, a change in air pressure, a change in humidity, a change in light conditions, a change in insolation, a change in gravity, a change electromagnetic fields, a change in radiation, and a change of ambient noise. The change of activity of the user and/or position of the body of the user may include change of one of activity of the user and/or position of the body of the user: lying down, sitting, standing, stepping, jumping, swimming, yachting, sailing, skiing, skating, rolling, cycling, skateboarding, and running.

According to another example embodiment, a method for heart disease risk assessment is provided. The method may include providing, by a first sensor, a first signal indicative of HRV and respiration of a user. The method may further include providing, by a second sensor, a second signal indicative of HRV, respiration, and movement of the user. The method may include continuously determining, by a controller communicatively coupled to the first sensor and the second sensor and based on the first signal and the second signal, a state function, wherein the state function associated with coupling of the HRV and the respiration. The method may also include receiving, by the controller, an indication of one of a change of a body position of the user or a change of one or more external conditions. In response to the indication, the method may determine, by the controller, a shape or profile of the distortion of the state function, wherein the distortion is caused by the change of the body position or the change of the one or more external conditions. The method may include performing, by the controller, an analysis of the shape or profile of the distortion to determine at least one sign of a risk of a heart failure. In response to the determination of the at least one sign of the risk of the heart failure, the method may include providing, by the controller and via an alert unit communicatively coupled to the controller, at least one alert or message regarding the at least one sign of the risk of the heart failure.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and, in which.

DETAILED DESCRIPTION

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

The present disclosure provides methods and systems for heart disease risk assessment. Some embodiments of the present disclosure may provide an early detection of a heart failure in a human organism at an asymptomatic stage.

Some embodiments of the present disclosure may provide a wearable device for heart disease risk assessment. The wearable device can be used personally. The wearable device may provide, to a user, alerts concerning a risk of a heart failure, so that the user can take early measures, for example, getting tested during a clinical examination. The wearable device may be used by insurance companies for an estimate of the risk of developing diseases by a client. The wearable device may be used by athletes and sport organizations to monitor sensibility of the athletes to physical exercises and determine safety of the physical activity and an appropriateness of the training regime. The wearable device may be used by automobile companies to continuously monitor assessment of heart disease risk of a driver. The heart disease risk assessment can be provided to a car safety or security system. For example, the heart disease risk assessment data can be used by the car safety system to pro-actively determine a level of safety of a forthcoming driving trip based on current and predicted driver's health condition and forthcoming route, traffic, speed and time of day for the forthcoming driving trip. The car safety system may adjust the forthcoming route and speed based on the level of safety and the driver's health condition.

Embodiments of the present disclosure may allow performing a rigorous analysis of the HRV using one or more physiological signals measured from the human body. Embodiments of the present disclosure may allow reduction in uncertainty in the assessment of the boundaries of HRV as a measure of healthy conditions and unhealthy conditions of a human organism and, thereby, increasing the reliability of the assessment of the risk of heart failure, atrial fibrillation, and cardiac arrest, and other signs of development of one or more disorders in the human organism.

Figure 1:
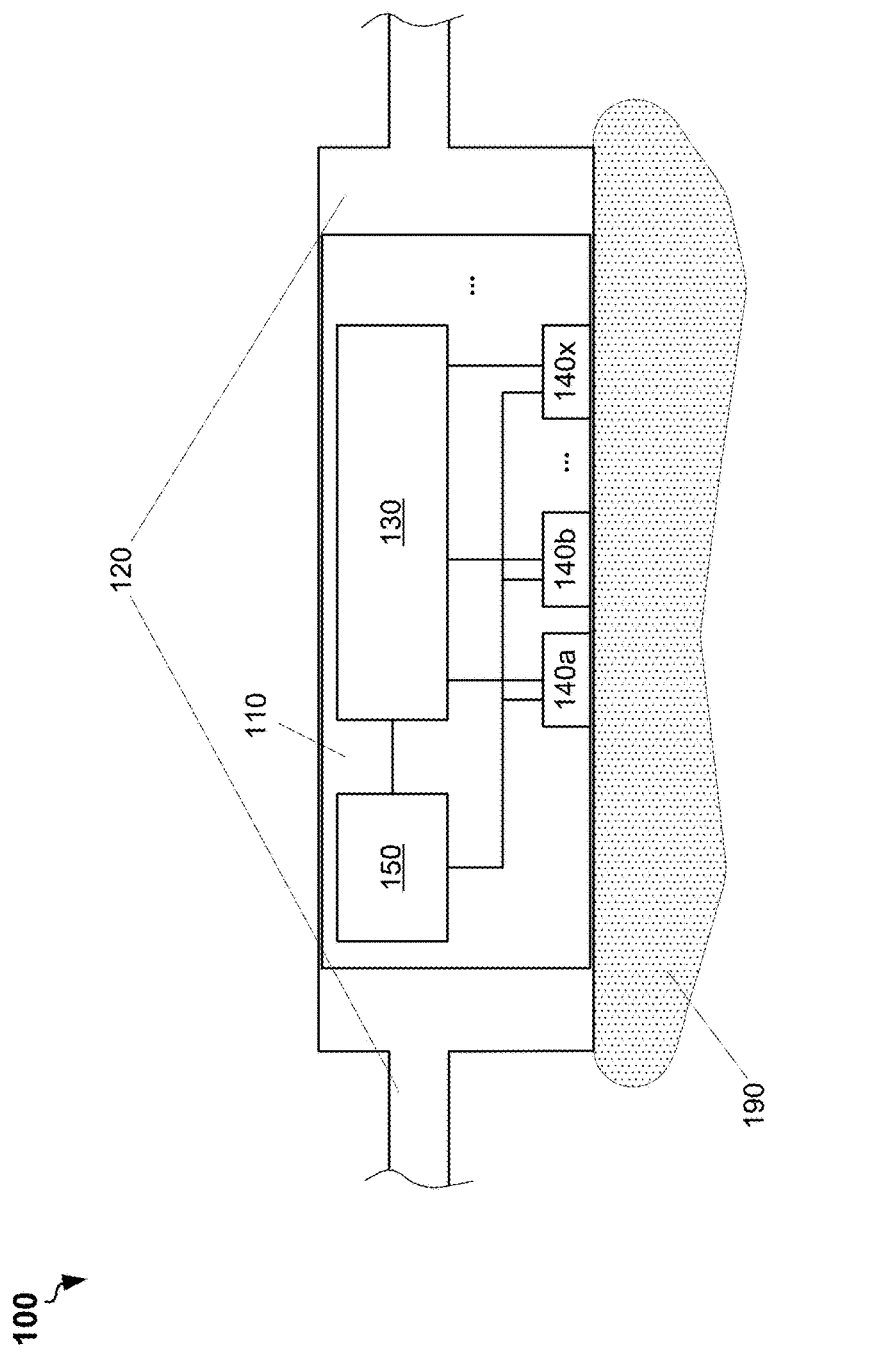
FIG. 1 is a schematic diagram showing an example wearable device for heart disease risk assessment, according to some embodiments of the present disclosure.

Referring now to the drawings, FIG. 1 is a schematic diagram showing an example wearable device 100 for heart disease risk assessment, according to some embodiments of the present disclosure. The wearable device may include a body 110 attached to a part 120. The part 120 may include a band, a bracelet, a strap configured to dispose the body 110 on a human body 190.

In one example embodiment, the part 120 may include a strap configured to be placed around a belt of the user. In another embodiment, the part 120 may include a strap configured to be positioned around a chest of the user. In yet another embodiment, the part 120 may include a strap, a bracelet, or a ring configured to be positioned around an ankle or a neck of the user. In other example embodiments, the body 110 can be integrated or configured to be attachable to a clothing of the user, for example a shirt, sock, pants, and so forth.

The body 110 of the wearable device 100 may include at least sensors 140a, 140b, . . . , 140x configured to sense signals representing physiological parameters of the human body 190. The body 110 may include a controller 130 configured to read and process the signals sensed by the sensors. The body 110 may further include a power supply 150 configured to provide power to the controller 130 and the sensors 140a, 140b, . . . , 140x.

Figure 2:
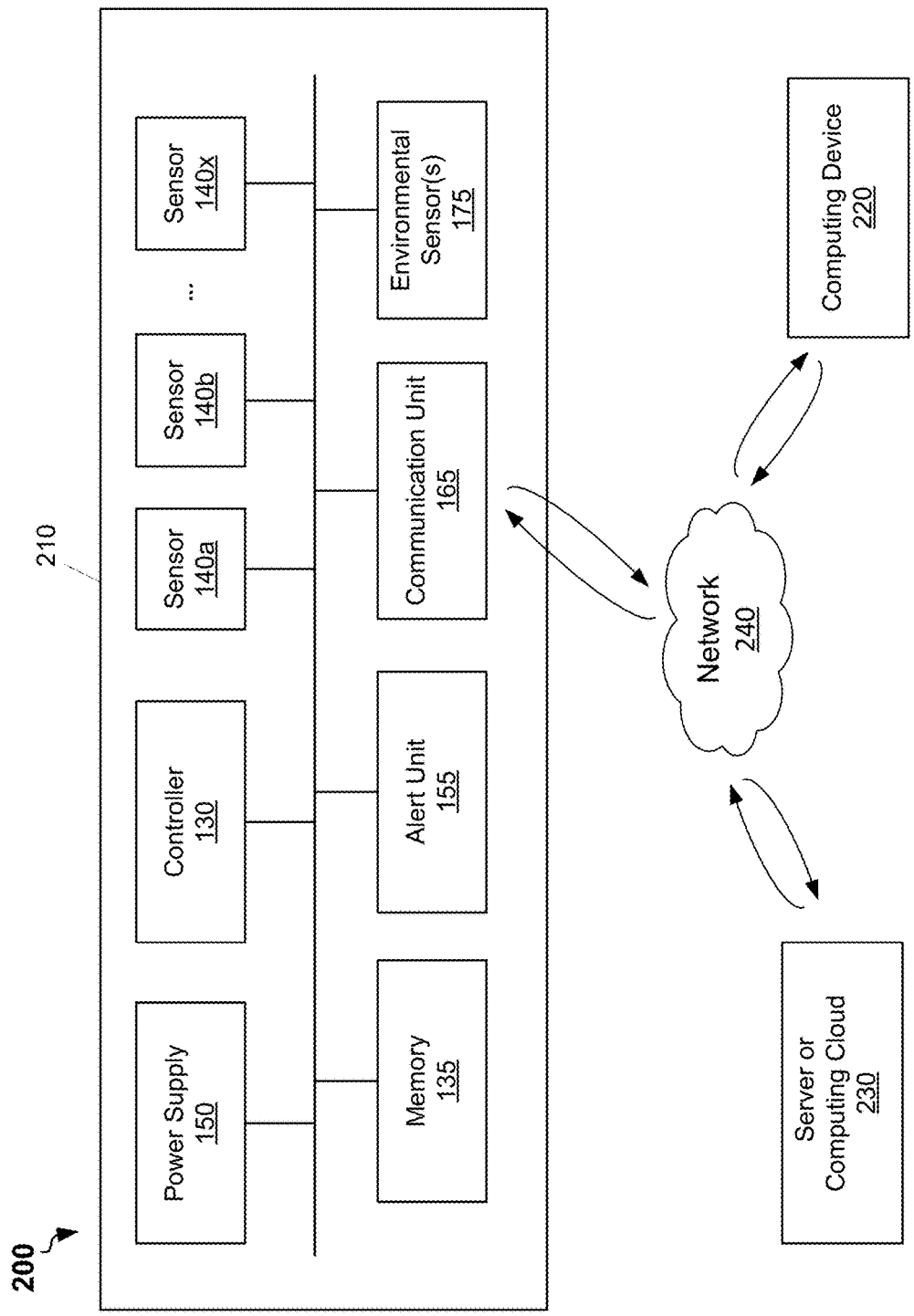
FIG. 2 is a block diagram of an environment, wherein methods for heart disease risk assessment can be implemented, according to some example embodiments.

FIG. 2 is a block diagram of environment 200, wherein methods for heart disease risk assessment can be implemented, according to some example embodiments. The environment 200 may include a system 210 for heart disease risk assessment. In some embodiments, the system 210 can be integrated into a wearable device as shown in FIG. 1. The system 210 may include sensors 140a, 140b, ..., and 140x. The sensors 140a, 140b, ..., 140x can be configured to sense signals indicative of vital signs and other medical parameters of the human body 190.

In some embodiments, the sensor 140a may be configured to sense a signal indicative of a heart rate and HRV of the user. The sensor 140a may include a photoplethysmography (PPG) sensor. The PPG sensor may be configured to detect a change in the reflected or transmitted intensity of respective color of the human body caused by the pressure pulse, volume pulse, blood flow, blood oxygen, or arterial wall distention changes when the heart pumps blood to periphery. For example, the change of the color intensity can be detected by illuminating the skin with light from a light-emitting diode and then measuring the amount of light either transmitted or reflected to a photodiode. The PPG sensor may provide a PPG signal, which represents intensity of the light either transmitted or reflected from the tissue of the human body. In certain embodiments, the sensor 140a may include a bioimpedance (BI) sensor. The BI sensor may be configured to detect a change in electrical impedance of the human body caused by the pressure pulse, volume pulse, blood flow, blood oxygen, or arterial wall distention changes when the heart pumps blood to periphery. The BI sensor may provide a BI signal. The BI signal represents resistivity dependence on blood flow conductivity (a blood velocity component) in the body when high frequency (e.g., 50-100 kHz) current transferred through the tissues of the human body. The PPG signal and BI signal may include pulse waveforms related to heart and respiration activities of the user.

In some embodiments, the sensor 140b can be configured to sense a signal indicative of breathing of the user. The sensor 140b may include a motion sensor for detecting motion of the human body 190. For example, the motion sensor may include a 3-axis accelerometer and/or a 3-axis gyroscope. The signal from the motion sensor can be analyzed by the controller 130 to determine a frequency (respiration rate) corresponding to breathing of the user. In some embodiments, the signal from the motion sensor can be analyzed to determine a respiration signal including respiration waveforms. The signal from the motion sensor can be analyzed by the controller 130 to determine a heart rate corresponding to heart activities of the user. In some embodiments, the signal from the motion sensor can be analyzed to determine a heart rate signal including HRV waveforms. The signal from the motion sensor can be also analyzed to detect movement of the user and the position of the body of the user. For example, the controller 130 can be configured to analyze the signal from motion sensor to detect whether the user is lying down, sitting, standing, stepping, walking upstairs, jumping, running, cycling, swimming and so forth.

In some embodiments, the sensors 140a, 140b, ..., and 140x may include an electrocardiogram (ECG) sensor to provide an ECG signal measured from the skin of the human body. The ECG signal can be used as a signal indicative of heart rate and HRV of the user.

In some embodiments, the system 210 may further include environmental sensors 175 for measuring changes in environmental conditions. For example, the environmental sensors 175 may include an ambient temperature sensor, an altitude sensor, a proximity sensor, a barometer, a humidity sensor, an ambient light sensor, a tenzo sensor, an acoustic sensor, and so forth. The signals from the environmental sensors can be analyzed by controller 130 to detect a change in ambient temperature, a change in air pressure, a change in humidity, a change in light conditions, a change in insolation, and a change of ambient noise.

The system 210 may include a power supply 150. The power supply 150 may include a battery or a rechargeable battery for providing power to components of the system 210.

The system 210 may include a controller 130. In various embodiments, the controller 130 may be implemented as a hardware utilizing either a combination of microprocessor(s), specially designed application-specific integrated circuits (ASICs), programmable logic devices, or system on chip (SoC) configured to run an operation system and various applications. The controller 130 may be configured to analyze signals from the sensors 140a, 140b, ..., 140x and environmental sensors 175 to estimate heart disease risks. In some embodiments, the system 210 may include memory 135 to store sensor data, application data, and instructions to be executable by the controller 130.

The system 210 may further include a communication unit 165. The communication unit 165 may include a Global System for Mobile communications (GSM) module, a Wi-Fi™ module, a Bluetooth™ module, a near field communication module, and the like. The communication unit 165 can be configured to communicate with a data network 240 such as the Internet, a Wide Area Network (WAN), a Local Area Network (LAN), a cellular network, and so forth, to send a data, for example, sensor data and messages concerning the health condition of the user.

The system 210 may further include an alert unit 175. The alert unit 175 may include an audio device, for example, a beeper or a speaker, to provide sound alerts to the user. The alert unit 175 may also include a light indicator, for example, a LED configured to light different colors indicating a healthy or unhealthy condition of the user. The alert unit 175 may include a haptic device to provide an alert by applying forces, vibrations, or motions to the user. The alert unit 175 may include a graphical display system configured to provide messages regarding health conditions of the user.

The environment 200 may further include a computing device 220. The computing device may include a personal computer (PC), a laptop, a smartphone, a tablet PC, a personal wearable device, and so forth. The computing device 220 can be configured to receive, via the communication unit 165 and/or data network 240, sensor data from sensors of the system 210 and process the sensor data to estimate risk of heart diseases. In some embodiments, the signals from the sensors 140a, 140b, ..., 140x and environmental sensors 175 can be first pre-processed by the controller 130 and then sent to the computing device 220 for further analysis. The pre-processing of the signals may include transformation of the signal from analog to digital formats and filtering the signals to reduce or suppress noise and artifacts in the signals.

The environment 200 may further include a server or computing cloud 230. The server or computing cloud 230 can include computing resources (hardware and software) available at a remote location and accessible over the data network 240. The server or computing cloud 230 can be communicatively coupled to system 210 via the data network 240. The server or computing cloud 230 can be shared by multiple user(s). In certain embodiments, the server or computing cloud 230 may include one or more server farms/clusters including a collection of computer servers that can be co-located with network switches and/or routers.

The server or computing cloud 230 may be configured to receive, via the communication unit 165 and data network 240, sensor data form sensors of the system 210 and process the sensor data to estimate risk of heart disease. The signals from the sensors 140a, 140b, . . . , 140x and environmental sensors 175 can be first pre-processed by the controller 130 and then sent to the server or computing cloud 230 for further analysis. The pre-processing of the signals may include transformation of the signal from an analog to digital format and filtering the signals to reduce or suppress noise and artifacts in the signals.

The server or computing cloud 230 may be further configured, to provide results of analysis of the sensor data and warning messages to the user of the system 210 and other authorized users. The authorized users may monitor the result of analysis using one or more applications of computing devices associated with the authorized users. The authorized users may be associated with health care institutions, medical insurance companies, sport organizations, and so forth.

Figure 3:
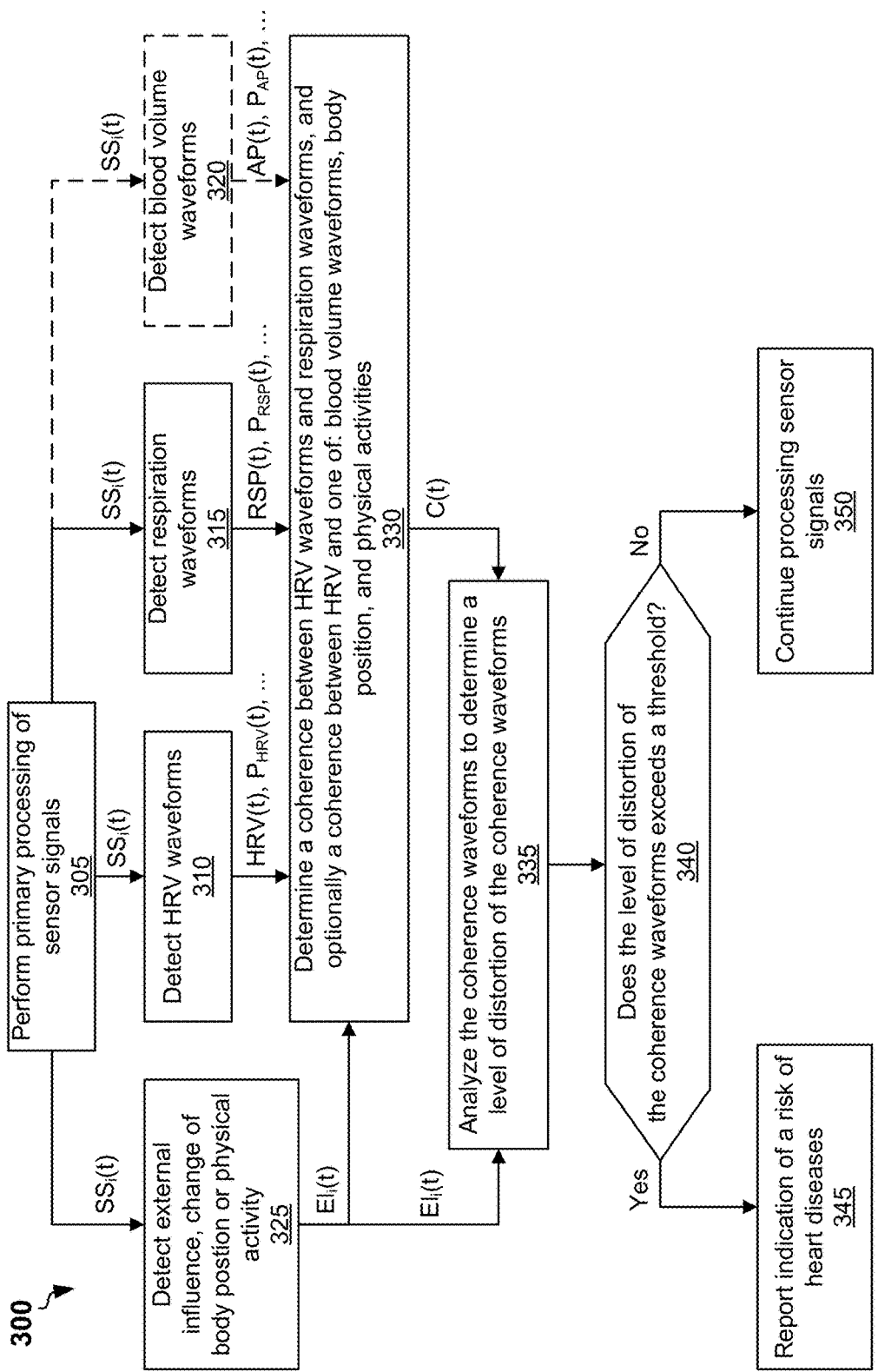
FIG. 3 is a flow chart of an example method for heart disease risk assessment, according to an example embodiment.

FIG. 3 is a flow chart of example method 300 for heart disease risk assessment, according to an example embodiment. The method 300 may be performed by system 210 of FIG. 2. The system 210 can be integrated in the wearable device 100 of FIG. 1. The wearable device 100 can be worn by a user. Below recited operations of method 300 may be implemented in an order different than described and shown in the figure. Moreover, method 300 may have additional operations not shown herein, but which can be evident to those skilled in the art from the present disclosure. Method 300 may also have fewer operations than outlined below and shown in FIG. 3.

The method 300 may commence in block 305 with performing, by a controller 130, primary processing of the sensor signals. The sensor signals may include a first signal measured by the sensor 140a. The first signal may be indicative of heart rate, HRV, and respiration of the user. The sensor signals may include a second signal measured by the sensor 140b. The second signal may also be indicative of heart rate, HRV, respiration of the user. The primary processing may include converting the sensor signals from an analog to digital format and filtering the signals to remove or suppress noise and artifacts in the sensor signals. The primary processing may further include normalizing and smoothing the sensor signals. Output of the primary processing may include a set of processed sensor signals $SS_i(t)$ (i=1, . . . , x).

In block 310, the method 300 may detect HRV waveforms in the processed sensor signals $SS_i(t)$ (i=1, . . . , x). The detection of HRV waveforms may include determining, based on the processed sensor signal $SS_i(t)$ (i=1, . . . , x), a pulse signal PLS(t) representing the pulse rate as a function of time. The method 300 may include determination, based on the pulse signal, HRV signal HRV(t). The method may further include determination, based on the pulse signal, of the following signals: power $P_{PLS}(t)$ of the pulse signal, amplitude $A_{PLS}(t)$ of the pulse signal, a crest factor $$CF_{PLS}(t) = \frac{A_{PLS}(t)}{std(P_{PLS}(t))}$$

of the pulse signal, and an amplitude spectrum $S_{PLS}(f)=|FFT(S_{PLS}(f))|$. The obtained signals HRV(t), PLS(t), $P_{PLS}(t)$, $A_{PLS}(t)$, $CF_{PLS}(t)$, and $S_{PLS}(f)$ can be further filtered to reduce noise and artifacts in the signals.

In block 315, the method 300 may detect respiration waveforms in the processed sensor signals $SS_i(t)$ (i=1, . . . , x). The detection of respiration waveforms may include determination, based on the processed signals $SS_i(t)$ (i=1, . . . , x), a respiration signal RSP(t). The method 300 may also include determination, based on the respiration signal, the following signals: power $P_{RSP}(t)$ of the respiration signal, an amplitude $A_{RSP}(t)$ of the respiration signal, a crest factor $$CF_{RSP}(t) = \frac{A_{RSP}(t)}{std(P_{RSP}(t))}$$

of the respiration signal, and an amplitude spectrum $S_{RSP}(f)=|FFT(S_{RSP}(f))|$ of the respiration signal. The obtained signals RSP(t), $P_{PRS}(t)$, $A_{RSP}(t)$, $CF_{RSP}(t)$, and $S_{RSP}(f)$ can be further filtered to reduce noise and artifacts in the signals.

Figure 4:
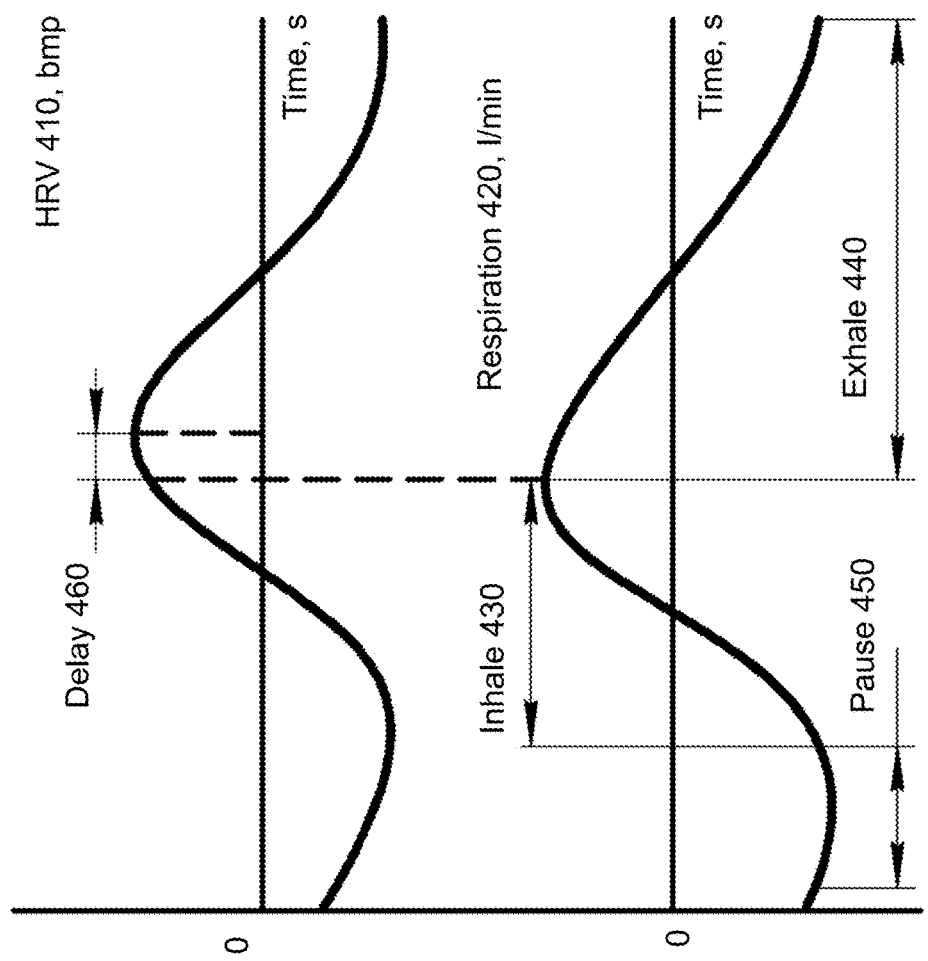
FIG. 4 shows a plot of example HRV waveform and example respiration waveform according to an example embodiment.

FIG. 4 shows plot 400 of example HRV waveform 410 and example respiration waveform 420, according to an example embodiment. The respiration waveform 420 can include the following components: a pause 450, an inhale 430, and an exhale 440. It is known that HRV bradycardiac and tachycardiac components can be coherent to components of the respiration waveforms. The coherence, a gain and a phase of coherence, may vary in different conditions. Under normal resting conditions, there is a regular delay (phase) 460 between the respiration waveform and the HRV waveform.

Referring back to FIG. 3, in optional block 320, the method 300 may detect pulse volume waveforms in the processed sensor signals $SS_i(t)$ (i=1, . . . , x). The method 300 may determine, based on the processed sensor signals $SS_i(t)$ (i=1, . . . , x), pulse volume signal AP(t) representing a function of blood pressure of the user of time. The method 300 may also determine, based on the pulse volume signal, the following signals: power $P_{AP}(t)$ of the pulse volume signal, an amplitude $A_{AP}(t)$ of the pulse volume signal, a crest factor $$CF_{AP}(t) = \frac{A_{AP}(t)}{std(P_{AP}(t))}$$

of the pulse volume signal, and an amplitude spectrum $S_{AP}(f)=|FFT(S_{AP}(f))|$ of the pulse volume signal. The obtained signals AP(t), $P_{AP}(t)$, $A_{AP}(t)$, $CF_{AP}(t)$, and $S_{AP}(f)$ can be further filtered to reduce noise and artifacts in the signals.

In block 325, the method 300 may detect, by the controller 130, an indication of external influence on the user, change in body position of the user, or change in in the physical activity of the user. For example, the method 300 may analyze, by the controller 130, the processed signals $SS_i(t)$ (i=1, . . . , x) and signals from environmental sensors 175 to extract signals $EI_i(t)$ representing changes in environmental conditions that may influence blood volume, respiration, heart rate and other vital signs and characteristic of body of the user. For example, the signals $EI_i(t)$ may represent a change in an ambient temperature, change in air pressure, change in humidity, change in lighting conditions, change in insolation, change in amount and spectrum of ambient noise, change in amount and spectrum of ambient sounds, change in spectrum of solar light, a change in electromagnetic fields, a change in radiation, and so forth. The signals $EI_i(t)$ may also represent change in position of body of the user, change in position of a part of the body of the user, and change in physical activity of user, such as lying down, sitting, standing, walking, stepping up and down, jumping, swimming, yachting, sailing, skiing, skating, rolling, cycling, skateboarding, and running.

It is known that external influence may cause temporal distortion of the coherence between the HRV waveforms and the respiration waveforms. A regulatory system of human organism adapts frequency of heart beats to the respiration rate and, thereby, restores the coherence between the HRV waveforms and the respiration waveforms. If a person suffers a heart failure, the regulatory system may not adapt the respiration, the frequency of cardiac cycles and volume of pumped blood to changes of environmental conditions. A reaction of a healthy human organism and unhealthy human organism to the same external influence can be different.

In block 330, the method 300 may determine a coherence between HRV waveforms and respiration waveforms. Optionally, the method 300 may determine a coherence between HRV waveforms and blood volume waveforms and a coherence between the respiration waveforms and the blood volume waveforms. The method 300 may determine a coherence between HRV waveforms and blood pressure waveforms and a coherence between the respiration waveforms and the blood pressure waveforms. The method 300 may include determination of a coherence between the HRV signal HRV(t) and the respirations signal RSP(t). The method 300 may include determination of energy of the coherence and a phase of the coherence. In some embodiments, coherences can be calculated for one or more pairs of signals x(t) and y(t), wherein the signals x(t) can be selected from signals HRV(t), $P_{PLS}(t)$, $A_{PLS}(t)$, $CF_{PLS}(t)$, and $S_{PLS}(f)$ related to heart rate of the user and the signal y(t) can be a corresponding signal selected from the signals RSP(t), $P_{PRS}(t)$, $A_{RSP}(t)$, $CF_{RSP}(t)$, and $S_{RSP}(f)$ related to respiration of the user. In the pairs of signals x(t) and y(t), the signal x(t) can be selected from the signals HRV(t), $P_{PLS}(t)$, $A_{PLS}(t)$, $CF_{PLS}(t)$, and $S_{PLS}(f)$ and the signal y(t) can be a corresponding signal selected from the signals AP(t), $P_{AP}(t)$, $A_{AP}(t)$, $CF_{AP}(t)$, and $S_{AP}(f)$ related to blood volume or blood pressure of the user Additional pairs of signals x(t) and y(t) may include the signal x(t) selected from the signals RSP(t), $P_{PRS}(t)$, $A_{RSP}(t)$, $CF_{RSP}(t)$, and $S_{RSP}(f)$ and the signal y(t) selected from the corresponding signals AP (t), $P_{AP}(t)$, $A_{AP}(t)$, $CF_{AP}(t)$, and $S_{AP}(f)$. In some embodiments, the method 300 may determine a coherence between the HRV signal HRV(t) and one or more signals $EI_i(t)$ representing change in the position of body of the user, change in the position of a part of the body of the user, or change in the physical activity of user.

A coherence between two signals can be determined in either time domain or frequency domain. For example, the coherence between the signal x(t) and the signal y(t) can be estimated by formula $$C_{xy}(f) = \frac{|G_{xy}(f)|^2}{G_{xx}(f) \cdot G_{yy}(f)},$$

wherein $G_{xy}(f)$ is cross-spectral density of the signals x(t) and y(t), $G_{xx}(f)$ is auto spectral density of the signal x(t), and $G_{yy}(f)$ is auto spectral density of signal y(t). In some embodiments, the coherence between signals x(t) and y(t) can be determined using a partial directed coherence.

A coherence between signals x(t) and y(t) can be determined based on shift in phases of the signals x(t) and y(t) or a time delay between the signals x(t) and y(t). For example, the coherence can be determined as $C_\varphi(t)=\arg(x(t))-\arg(y(t))$, wherein arg(x(t)) is instant phase of the signal x(t) and arg(y(t)) is instant phase of the signal y(t). A coherence between signals x(t) and y(t) can be also determined as $C_\tau(t)=\tau_x-\tau_y$, wherein $\tau_x$ and $\tau_y$ are time positions of characteristic points (for example, minimums, maximums, and zero crossings) of the signals x(t) and y(t), respectively. Coherence between signals x(t) and y(t) can be also determined by their correlation function $R_{xy}(\tau)=(x(t),y(t+\tau))$.

As result, one or more coherences signals $C_1(t)$, $C_2(t)$, ... $C_n(t)$ between heart rate related signals, respiration related signals, and, optionally, blood pressure related signals can be estimated using different methods for calculation of the coherence. The coherences signals $C_1(t)$, $C_2(t)$, ... $C_n(t)$ can be further filtered to reduce noise and artifacts in the signals.

Figure 5:
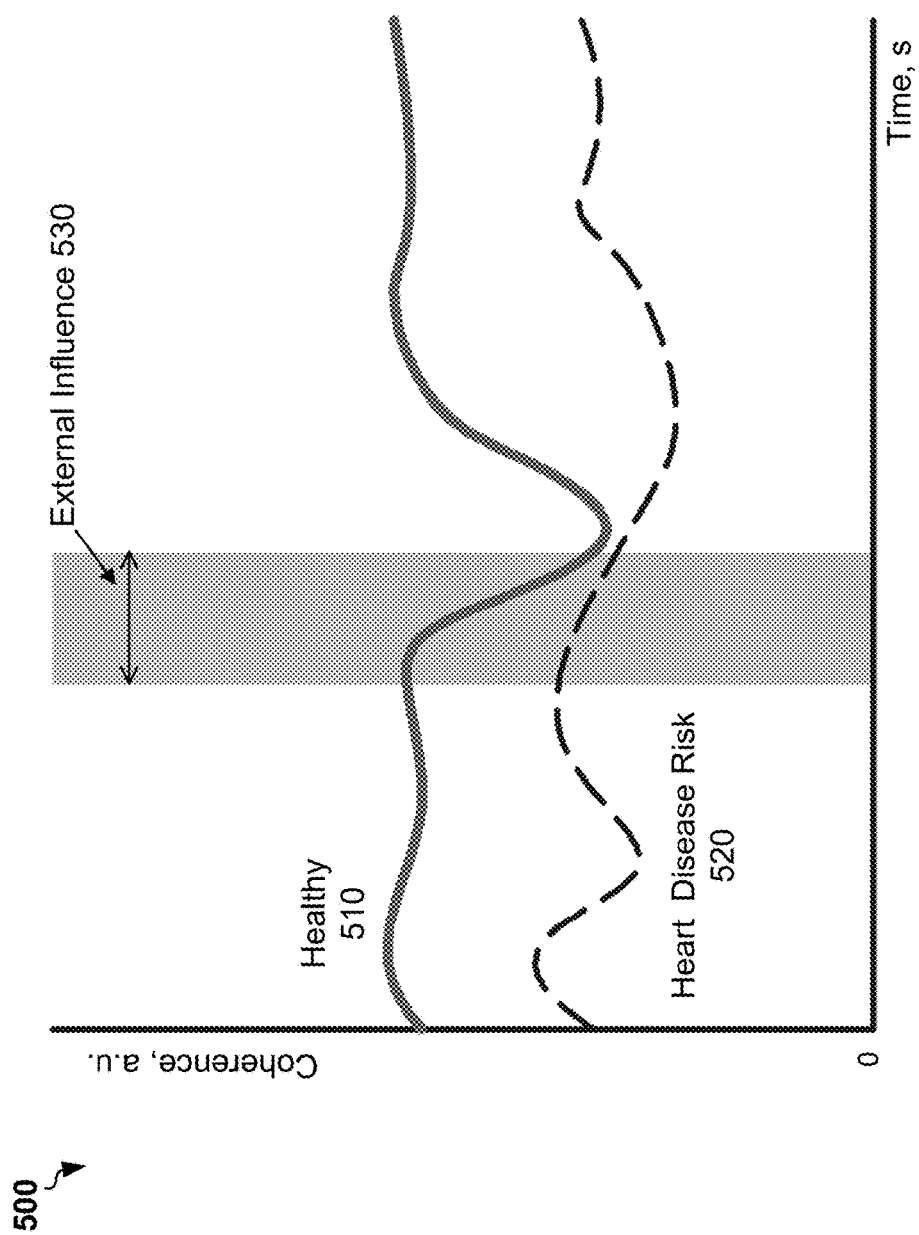
FIG. 5 shows a plot of coherence of HRV waveforms with respect to a respiration waveforms for a healthy person and a person with a heart disease risk, according to example embodiment.

FIG. 5 shows a plot of a coherence (phase and energy) 510 between HRV waveforms and respiration waveforms of a healthy person and a coherence (phase and energy) 520 between HRV waveforms and respiration waveforms of a person experiencing a heart failure, according to an example embodiment. After an external influence 530 occurs, the shape of the coherences 510 and 520 are distorted. The shape of a distortion of the coherence 520 corresponding to the person suffering from a heart failure differs from the shape of distortion of the coherence 510 corresponding to a healthy person.

Referring back to FIG. 3, the method 300 may analyze, in block 335, the coherence C(t) (phase and energy) to determine a level of distortion of the coherence (phase and energy) after the external influence has been detected. The level of distortion can be calculated using one or more metrics in the function space.

The coherence C(t) may include a linear combination of coherence signals $C_1(t)$, $C_2(t)$, ... $C_n(t)$ obtained in block 330. The coherence C(t) can include a vector of some of the coherence signals $C_1(t)$, $C_2(t)$, ... $C_n(t)$. To determine a level of (D) of coherence the coherence C(t) can be compared to a "normal" coherence $C_{norm}(t)$. The "normal" coherence $C_{norm}(t)$ may represent coherence for a healthy person obtained during the same external influence. The comparison may include comparison of amplitudes, energies, spectra, shapes, and duration of signals after the external influence occurs. The "normal" coherence $C_{norm}(t)$ may be determined based on population studies under the same external influence. The "normal" coherence can be adjusted for a particular person and/or a type, duration, and amount of the external influence. If the coherence C(t) represents a vector, then the comparison can be carried out for each projection of the vector, determine a difference vector D.

In block 340, the method 300 may determine that the level of distortion of the coherence (phase and energy) exceeds a threshold. The threshold can be determined based on a shape of distortion of the coherence (phase and energy) between the HRV waveforms and the respiration waveforms measured for the healthy person. The threshold can depend on a type and amount of external influence, for example, an amount of the change in the external noise, amount of change in the ambient temperature, and so forth. If the level of distortion of the coherence (phase and energy) exceeds the threshold, it may be indicative of the user experiencing a pathological process leading to the heart failure. The pathological process leading to the heart failure may be an outcome of development of one or more diseases, such as heart diseases, vascular diseases, kidney diseases, lung diseases, diabetes, and so forth.

If the coherence C(t) represents a vector, then the difference vector D can be compared to vector T of thresholds $T_1, \ldots, T_n$. If one or more component of the difference vector D exceeds by a pre-determined percentage a corresponding component of the vector T', than the method 500 may proceed to block 345.

In block 345, in response to determination that the level of distortion of the coherence (phase and energy) exceeds the threshold, the method 300 may issue an alert or a warning message concerning a sign of a risk to the heart failure. For example, the method 300 may provide, via the alert unit 175, a sound alert or display a warning message on a graphical display system of the system 210. In some embodiments, the method 300 may a message regarding a confidence of the determination of the risk of the heart failure to be issued. The confidence can be based on quality of the signals used to determine the coherence C(T). The quality of the signals can be determined based on a signal-to-noise ratio of the signals. In block 350, the method 300 may continue with processing next portions of sensor signals measured by sensors 140a and 140b.

Figure 6:
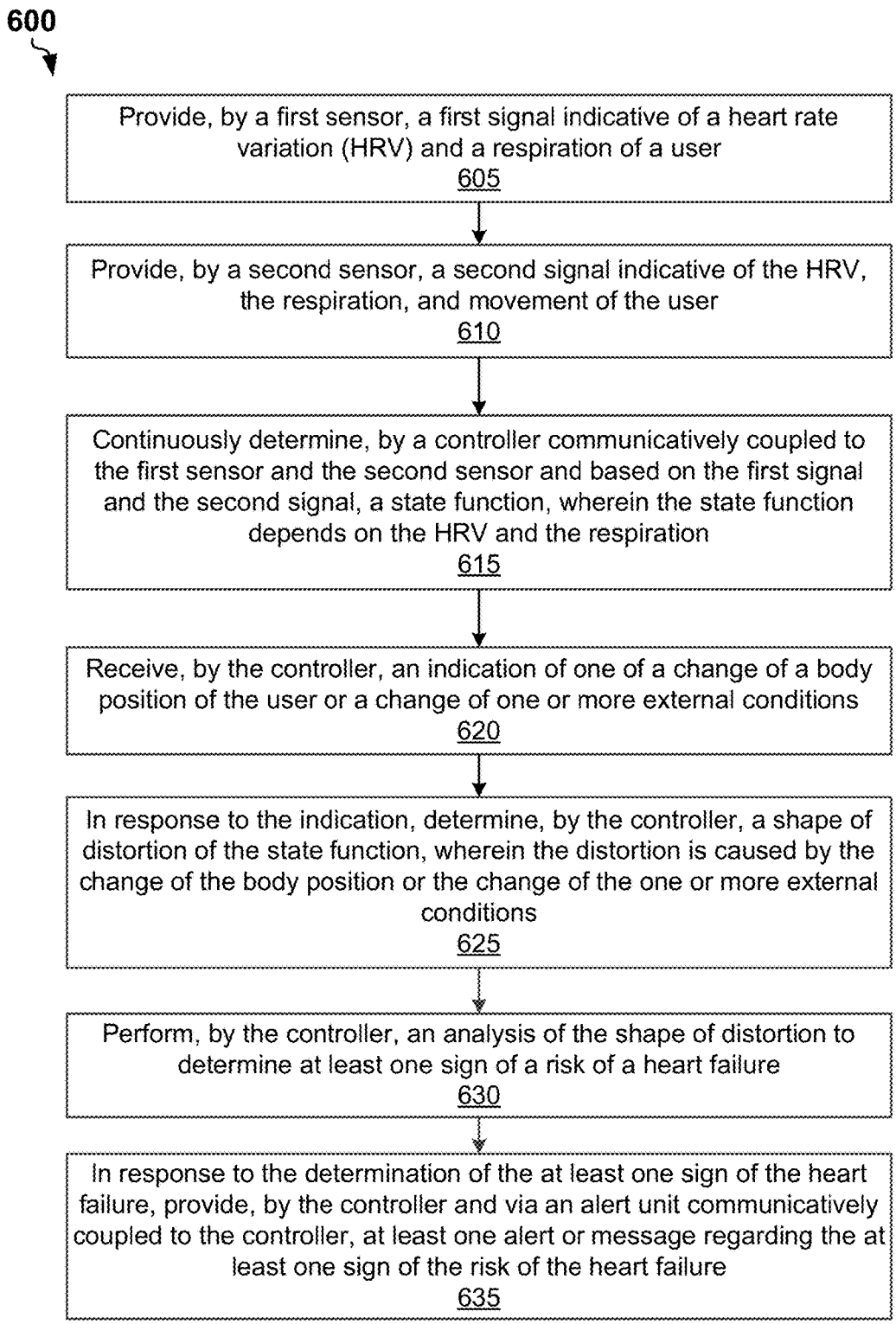
FIG. 6 is a flow chart of example method for heart disease risk assessment, according to some example embodiments.

FIG. 6 is a flow chart of an example method 600 for heart disease risk assessment, according to some other example embodiments. The method 600 may be performed by elements of system 210 of FIG. 2. The system 210 can be integrated in the wearable device 100 of FIG. 1. The wearable device 100 can be worn by a user. Below recited operations of method 600 may be implemented in an order different than described and shown in the figure. Moreover, method 600 may have additional operations not shown herein, but which can be evident to those skilled in the art from the present disclosure. Method 600 may also have fewer operations than outlined below and shown in FIG. 6.

The method 600 commence, in block 605, with providing, by a first sensor, a first signal indicative of a heart rate variability (HRV) of a user. The first sensor may include a PPG sensor configured to be in contact with a body of the user and the first signal may include a PPG signal including a HRV component and a respiration component.

In block 610, the method 600 may include providing, by a second sensor, a second signal indicative of movements of the user. The movements can be related to the HRV and physical activity of the user. The second sensor may include a motion sensor configured to detect movements related to the HRV. The second sensor may include a motion sensor configured to detect body motions related to the physical activity of the user. The motion sensor may include an accelerometer or a gyroscope. The first sensor and the second sensor can be integrated in a wearable device configured to be disposed on a body of the user.

In block 615, the method 600 may continuously determine, by a controller communicatively coupled to the first sensor and the second sensor and based on the first signal and the second signal, a state function. The state function may depend on the HRV, the respiration, and motions. For example, the state function may include a coherence of the HRV with respect to the respiration. The state function may also include a coherence of the HRV with respect to the physical activity of the user.

In block 620, the method 600 may receive, by the controller, an indication of one of a change of a body position of the user or a change of one or more external conditions. The change of one or more external conditions may include one of the following: a change in the ambient temperature, change in air pressure, change in humidity, change in light conditions, change in insolation, and change in ambient noise. The change of the position of the body of the user may include change of one of positions of the body of the user: lying down, sitting, standing, stepping, jumping, and running.

In block 625, in response to the indication, the method 600 may determine, by the controller, a shape of distortion of the state function. The distortion can be caused by the change in the body position or the change of the one or more external conditions.

In block 630, the method 600 may perform, by the controller, an analysis of the shape of distortion to determine at least one sign of a risk to the heart failure. The analysis may include determining, by the controller and based on the shape of distortion, a level of distortion of the state function and comparing the level of distortion to a threshold. The threshold can be determined based on a shape of distortion of a state function measured for the healthy person.

In block 635, in response to the determination of the at least one sign of a risk to the heart failure, the method 600 may be providing, by the controller and via an alert unit communicatively coupled to the controller, at least one alert or message regarding the at least one sign of a risk to the heart failure.

Figure 7:
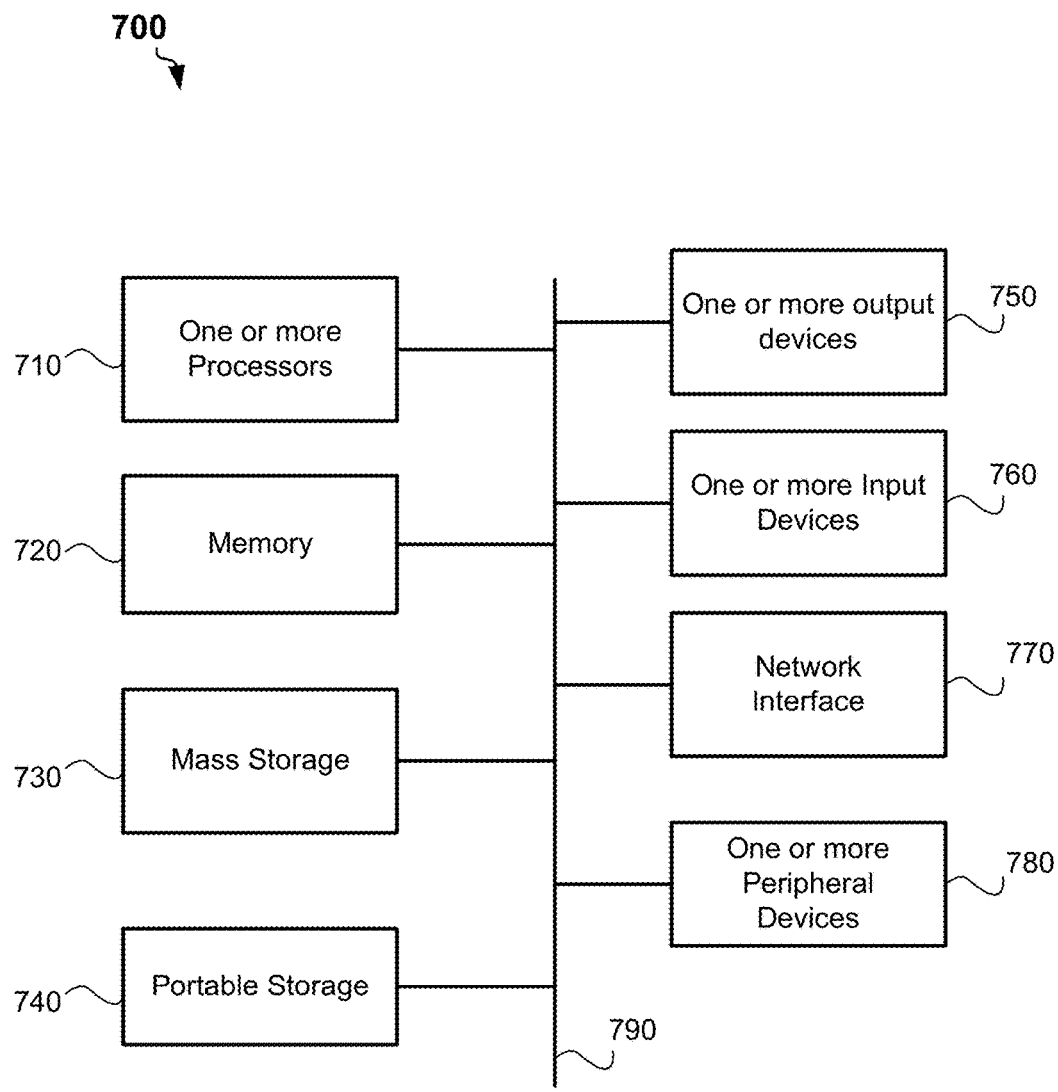
FIG. 7 shows a computing system that can be used to implement a method for heart disease risk assessment, according to an example embodiment.

FIG. 7 illustrates an exemplary computing system 700 that may be used to implement embodiments described herein. The exemplary computing system 700 of FIG. 7 may include one or more processors 710 and memory 720. Memory 720 may store, in part, instructions and data for execution by the one or more processors 710. Memory 720 can store the executable code when the exemplary computing system 700 is in operation. The exemplary computing system 700 of FIG. 7 may further include a mass storage 730, portable storage 740, one or more output devices 750, one or more input devices 760, a network interface 770, and one or more peripheral devices 780.

The components shown in FIG. 7 are depicted as being connected via a single bus 790. The components may be connected through one or more data transport means. The one or more processors 710 and memory 720 may be connected via a local microprocessor bus, and the mass storage 730, one or more peripheral devices 780, portable storage 740, and network interface 770 may be connected via one or more input/output buses.

Mass storage 730, which may be implemented with a magnetic disk drive or an optical disk drive, is a non-volatile storage device for storing data and instructions for use by a magnetic disk or an optical disk drive, which in turn may be used by one or more processors 710. Mass storage 730 can store the system software for implementing embodiments described herein for purposes of loading that software into memory 720.

Portable storage 740 may operate in conjunction with a portable non-volatile storage medium, such as a compact disk (CD) or digital video disc (DVD), to input and output data and code to and from the computing system 700 of FIG. 7. The system software for implementing embodiments described herein may be stored on such a portable medium and input to the computing system 700 via the portable storage 740.

One or more input devices 760 provide a portion of a user interface. The one or more input devices 760 may include an alphanumeric keypad, such as a keyboard, for inputting alphanumeric and other information, or a pointing device, such as a mouse, a trackball, a stylus, or cursor direction keys. Additionally, the computing system 700 as shown in FIG. 7 includes one or more output devices 750. Suitable one or more output devices 750 include speakers, printers, network interfaces, and monitors.

Network interface 770 can be utilized to communicate with external devices, external computing devices, servers, and networked systems via one or more communications networks such as one or more wired, wireless, or optical networks including, for example, the Internet, intranet, LAN, WAN, cellular phone networks (e.g., Global System for Mobile communications network, packet switching communications network, circuit switching communications network), Bluetooth radio, and an IEEE 802.11-based radio frequency network, among others. Network interface 770 may be a network interface card, such as an Ethernet card, optical transceiver, radio frequency transceiver, or any other type of device that can send and receive information. Other examples of such network interfaces may include Bluetooth®, 3G, 4G, and WiFi® radios in mobile computing devices as well as a USB.

One or more peripheral devices 780 may include any type of computer support device to add additional functionality to the computing system. The one or more peripheral devices 780 may include a modem or a router.

The components contained in the exemplary computing system 700 of FIG. 7 are those typically found in computing systems that may be suitable for use with embodiments described herein and are intended to represent a broad category of such computer components that are well known in the art. Thus, the exemplary computing system 700 of FIG. 7 can be a personal computer, hand held computing device, telephone, mobile computing device, workstation, server, minicomputer, mainframe computer, or any other computing device. The computer can also include different bus configurations, networked platforms, multi-processor platforms, and so forth. Various operating systems (OS) can be used including UNIX, Linux, Windows, Macintosh OS, Palm OS, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the example embodiments. Those skilled in the art are familiar with instructions, processor(s), and storage media.

It is noteworthy that any hardware platform suitable for performing the processing described herein is suitable for use with the example embodiments. The terms "computer-readable storage medium" and "computer-readable storage media" as used herein refer to any medium or media that participate in providing instructions to a CPU for execution. Such media can take many forms, including, but not limited to, non-volatile media, volatile media, and transmission media. Non-volatile media include, for example, optical or magnetic disks, such as a fixed disk. Volatile media include dynamic memory, such as RAM. Transmission media include coaxial cables, copper wire, and fiber optics, among others, including the wires that include one embodiment of a bus. Transmission media can also take the form of acoustic or light waves, such as those generated during radio frequency and infrared data communications. Common forms of computer-readable media include, for example, a floppy disk, a flexible disk, a hard disk, magnetic tape, any other magnetic medium, a CD-read-only memory (ROM) disk, DVD, any other optical medium, any other physical medium with patterns of marks or holes, a RAM, a PROM, an EPROM, an EEPROM, a FLASHEPROM, any other memory chip or cartridge, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Thus, systems and methods for heart disease risk assessment are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A system for heart disease risk assessment, the system comprising:
    a first sensor configured to provide a first signal indicative of a heart rate variation (HRV) and respiration of a user;
    a second sensor configured to provide a second signal indicative of the HRV, movement and a physical activity of the user; and
    a controller communicatively coupled to the first sensor and the second sensor, wherein the controller is configured to:
        continuously determine, based on the first signal and the second signal, a state function, wherein the state function depends on the HRV and the respiration;
        receive an indication of one of a change of a body position or the physical activity of the user or a change of one or more external conditions;
        in response to the indication, determine a shape of a distortion of the state function, wherein the distortion is caused by the change in the body position or the physical activity of the user or the change in the one or more external conditions;
        perform an analysis of the shape of the distortion to determine at least one sign of a risk of heart failure; and
        in response to the determination of the at least one sign of the risk of heart failure, provide, via an alert unit communicatively coupled to the controller, at least one alert or message regarding the at least one sign of the risk of heart failure.

2. The system of claim 1, wherein the state function includes a coherence of the HRV with respect to the respiration.

3. The system of claim 1, wherein the first sensor includes a photoplethysmography (PPG) sensor configured to be contactable with a body of the user and the first signal includes a PPG signal indicative of HRV and breathing.

4. The system of claim 1, wherein the first sensor includes a bioimpedance (BI) sensor configured to be contactable with a body of the user and the first signal includes a BI signal indicative of HRV and breathing.

5. The system of claim 1, wherein the second sensor includes one or more of an accelerometer and a gyroscope configured to detect the HRV, the breathing, the movement, and the physical activity of the user.

6. The system of claim 1, wherein the first sensor and the second sensor are integrated into a wearable device, the wearable device being configured to be disposed on a body of the user.

7. The system of claim 1, wherein the analysis includes:
   determining, based on the shape of distortion, a level of the distortion of the state function; and
   comparing the level of distortion to a threshold.

8. The system of claim 7, wherein the threshold is determined based on a shape of distortion of a state function measured for a healthy person.

9. The system of claim 1, wherein the change of one or more external conditions includes one of the following: a change in ambient temperature, a change in air pressure, a change in humidity, a change in light conditions, a change in insolation, and a change of ambient noise.

10. The system of claim 1, wherein the change of position of the body or the physical activity of the user includes change of one of positions of the body of the user: lying down, sitting, standing, stepping, jumping, and running.

11. A method for heart disease risk assessment, the method comprising:
   providing, by a first sensor, a first signal indicative of a heart rate variation (HRV) and respiration of a user;
   providing, by a second sensor, a second signal indicative of the HRV, movement, and physical activity of the user; and
   continuously determining, by a controller communicatively coupled to the first sensor and the second sensor and based on the first signal and the second signal, a state function, wherein the state function depends on the HRV and the respiration;
   receiving, by the controller, an indication of one of a change of a body position or the physical activity of the user or a change of one or more external conditions;
   in response to the indication, determining, by the controller, a shape of distortion of the state function, wherein the distortion is caused by the change of the body position or the physical activity of the user or the change of the one or more external conditions;
   performing, by the controller, an analysis of the shape of distortion to determine at least one sign of a risk to the heart failure; and
   in response to the determination of the at least one sign of the risk to the heart failure, providing, by the controller and via an alert unit communicatively coupled to the controller, at least one alert or message regarding the at least one sign of the risk to the heart failure.

12. The method of claim 11, wherein the state function includes a coherence of the HRV with respect to the respiration.

13. The method of claim 11, wherein the first sensor includes a photoplethysmography (PPG)) sensor configured to be contactable with a body of the user and the first signal includes a PPG signal.

14. The method of claim 11, wherein the first sensor includes a bioimpedance (BI) sensor configured to be contactable with a body of the user and the first signal includes a BI signal.

15. The method of claim 11, wherein:
   the second sensor includes one or more of an accelerometer and a gyroscope configured to detect the HRV, the movement of the body of the user, the body position of the user, and the physical activity of the user; and
   the state function includes a coherence of HRV with respect to the body position of the user or the physical activity of the user.

16. The method of claim 11, wherein the first sensor and the second sensor are integrated in a wearable device, the wearable device being configured to be disposed on a body of the user.

17. The method of claim 11, wherein the analysis includes:
   determining, by the controller and based on the shape of distortion, a level of distortion of the state function; and
   comparing, the level of distortion to a threshold.

18. The method of claim 17, wherein the threshold is determined based on a shape of distortion of a state function measured for a healthy person.

19. The method of claim 11, wherein the change of one or more external conditions includes one of the following: a change in ambient temperature, a change in air pressure, a change in humidity, a change in light conditions, a change in insolation, and a change of ambient noise.

20. A system for heart disease risk assessment, the system comprising:
   a first sensor integrated in a wearable device and configured to provide a first signal informative of a heart rate variation (HRV) and respiration of a user, wherein the wearable device is configured to be disposed on a body of the user;
   a second sensor integrated in the wearable device and configured to provide a second signal indicative of a HRV, a body position of the user, and a physical activity of the user;
   a controller communicatively coupled to the first sensor and the second sensor, wherein the controller is configured to:
      continuously determine, based on the first signal and the second signal, a coherence of the HRV with respect to the respiration or a coherence of the HRV with respect to the body position of the user or the physical activity of the user;
      receive an indication of one of a change of the body position of the user, a change of the physical activity of the user, or a change of one or more external conditions;
      in response to the indication, determine a shape of distortion of the delay, wherein the distortion is caused by the change of the body position of the user, the change of the physical activity of the user, or the change of the one or more external conditions;
      determine, based on the shape of distortion, a level of distortion of the coherence; and
      determine that the level of distortion exceeds a threshold; and
   an alert unit configured to provide, in response to the determination that the level of distortion exceeds a threshold, at least one alert or message regarding a sign of risk of the heart failure.

* * * * *